US009918930B2

(12) United States Patent
Shirai et al.

(10) Patent No.: US 9,918,930 B2
(45) Date of Patent: Mar. 20, 2018

(54) PROCESSED NUTMEG PRODUCT AND METHOD FOR PRODUCING SAME

(71) Applicant: KAO CORPORATION, Tokyo (JP)

(72) Inventors: Tomohiro Shirai, Utsunomiya (JP);
Kentaro Kumihashi, Utsunomiya (JP);
Mitsuyoshi Sakasai, Kawasaki (JP);
Hiroshi Kusuoku, Shimotsuke (JP);
Hiroshi Hashimoto, Pathumwan (TH)

(73) Assignee: KAO CORPORATION, Tokyo (JP)

( * ) Notice: Subject to any disclaimer, the term of this patent is extended or adjusted under 35 U.S.C. 154(b) by 634 days.

(21) Appl. No.: 14/394,881

(22) PCT Filed: Jul. 11, 2013

(86) PCT No.: PCT/JP2013/068931
§ 371 (c)(1),
(2) Date: Oct. 16, 2014

(87) PCT Pub. No.: WO2014/010657
PCT Pub. Date: Jan. 16, 2014

(65) Prior Publication Data
US 2015/0071865 A1  Mar. 12, 2015

(30) Foreign Application Priority Data

Jul. 12, 2012 (JP) ................. 2012-156268
Jul. 4, 2013 (JP) ................. 2013-140593
Jul. 4, 2013 (JP) ................. 2013-140600

(51) Int. Cl.
| | |
|---|---|
| *A61K 8/97* | (2017.01) |
| *A61Q 11/00* | (2006.01) |
| *A61K 8/34* | (2006.01) |
| *A61Q 19/00* | (2006.01) |
| *A61Q 17/04* | (2006.01) |
| *A61K 36/185* | (2006.01) |

(52) U.S. Cl.
CPC ............. *A61K 8/97* (2013.01); *A61K 8/34* (2013.01); *A61K 36/185* (2013.01); *A61Q 11/00* (2013.01); *A61Q 17/04* (2013.01); *A61Q 19/00* (2013.01); *A61Q 19/004* (2013.01); *A61K 2236/00* (2013.01); *A61K 2800/244* (2013.01); *A61K 2800/74* (2013.01)

(58) Field of Classification Search
None
See application file for complete search history.

(56) References Cited

U.S. PATENT DOCUMENTS

| | | |
|---|---|---|
| 6,270,752 B1 | 8/2001 | Verona |
| 2004/0047930 A1 | 3/2004 | Webbe et al. |
| 2007/0031579 A1* | 2/2007 | Draanen .............. A23L 27/12 426/650 |
| 2011/0118346 A1 | 5/2011 | Hwang et al. |
| 2012/0083525 A1* | 4/2012 | Oh ..................... A61K 31/341 514/461 |

FOREIGN PATENT DOCUMENTS

| | | |
|---|---|---|
| CN | 102406557 A | 4/2012 |
| JP | 64-83023 | 3/1989 |
| JP | 1-153622 | 6/1989 |
| JP | 3-176413 | 7/1991 |
| JP | 4-337394 | 11/1992 |
| JP | 6-157259 A | 6/1994 |
| JP | 2001-163753 | 6/2001 |
| JP | 2001-520178 | 10/2001 |
| JP | 2011-500670 A | 1/2011 |
| JP | 2012-153617 | 8/2012 |
| JP | 2013-136733 | 7/2013 |
| WO | WO 2011/068813 A1 | 6/2011 |
| WO | 2013/080830 A1 | 6/2013 |

OTHER PUBLICATIONS

J.S. Pruthi, et al., Extraction of Pectin from Pericarp of Nutmeg (*Myristica fragrans*), China Academic Journal Electronic Publishing House, vol. 6, Jun. 30, 1987, pp. 50-51 and cover pages (with English translation of relevant portions).
Extended European Search Report dated Feb. 8, 2016 in Patent Application No. 13817462.8.
H.J. Kim et al., "Characterization of Antioxidants in Nutmeg (*Myristica fragrans* Houttuyn) Oil", In: "ACS Symposium Series", vol. 1035, XP-055245934, Jan. 1, 2010, pp. 239-252.
David D. McKemy, "Chapter 13 TRPM8: The Cold and Menthol Receptor", TRP Ion Channel Function in Sensory Transduction and Cellular Signaling Cascades, XP-055237826, Jan. 1, 2007, pp. 1-8.
International Preliminary Report on Patentability and Written Opinion dated Jan. 22, 2015 in PCT/JP2013/068931 (submitting English translation only).
International Search Report dated Oct. 15, 2013, in PCT/JP2013/068931, filed Jul. 11, 2013.
Gordon Reid, et al., "Ion channels activated by cold and menthol in cultured rat dorsal root ganglion neurones", Neuroscience Letters, vol. 324, 2002, pp. 164-168.
David D. McKemy, et al., "Identification of a cold receptor reveals a general role for TRP channels in thermosensation", Nature, vol. 416, Mar. 2002, pp. 52-58.
Andrea M. Peier, et al., "A TRP Channel that Senses Cold Stimuli and Menthol", Cell, vol. 108, Mar. 8, 2002, pp. 705-715.
H.-J. Behrendt, et al., "Characterization of the mouse cold-menthol receptor TRPM8 and vanilloid receptor type-1 VR1 using a (Continued)

*Primary Examiner* — Qiuwen Mi
(74) *Attorney, Agent, or Firm* — Oblon, McClelland, Maier & Neustadt, L.L.P.

(57) ABSTRACT

The present invention provides a processed plant product having an excellent TRPM8 activating action, a method for producing the same, and a cooling agent and a TRPM8 activator comprising the processed plant product. A method for producing a processed nutmeg product, comprising a step of simultaneously treating nutmeg or an extract thereof with an alcohol or a 25% (v/v) or more alcohol aqueous solution and one or more selected from a protonic acid and an H-type cation exchange resin.

17 Claims, 1 Drawing Sheet

(56) References Cited

OTHER PUBLICATIONS fluorometric imaging plate reader (FLIPR) assay", British Journal of Pharmacology, vol. 141, No. 4, 2004, pp. 737-745.

* cited by examiner

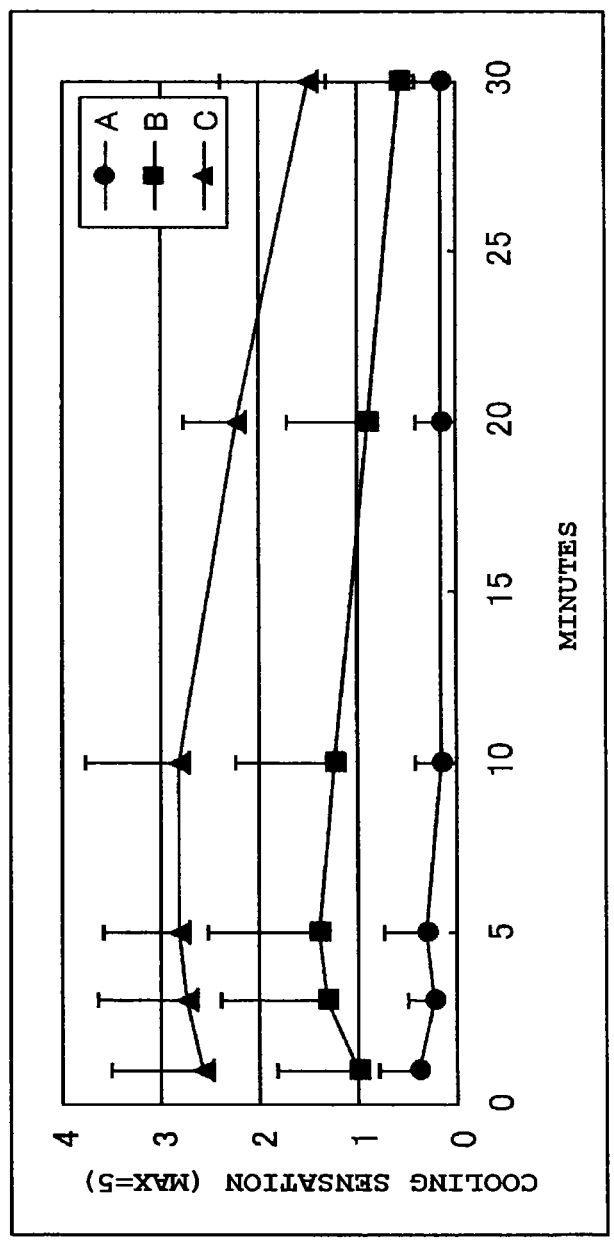

PROCESSED NUTMEG PRODUCT AND METHOD FOR PRODUCING SAME

FIELD OF THE INVENTION

The present invention relates to a processed nutmeg product, a method for producing the same, a cooling agent, a TRPM8 activator, a cosmetic and an oral composition.

BACKGROUND OF THE INVENTION

Nutmeg and the processed products thereof (such as nutmeg oil) are useful compounds having been used for, for example, gastrointestinal drugs, headache medicines, and spices since ancient times.

On the other hand, for the purpose of imparting refreshing feeling in use or after use, cool-feeling materials are frequently mixed in various products such as cosmetics, hair care products, toiletry products, bath additives and pharmaceuticals; and as such a cool-feeling material, menthol is widely used.

It is considered cooling sensation is imparted by menthol as a result of direct action of menthol on the sensory nerve ending present in the skin or the mucosal tissue, and the investigation of the mechanism of imparting cooling sensation has been advanced.

Of the sensory nerves of rat, the neuron generating the inward ionic current as a response to a weak cold stimulus has been found to exhibit a similar responsiveness to menthol (Non Patent Literature 1). On the basis of this finding, it has been revealed that the cooling sensation due to the stimulus of menthol is caused by an inward ionic current.

As a receptor exhibiting response to menthol and cold stimulus, CMR-1 (cold and menthol sensitive receptor) has been identified from trigeminal nerve neuron (Non Patent Literature 2). This receptor is referred to as TRPM8 (Non Patent Literature 3), and the receptor, which is an excitatory ion channel belonging to the TRP ion channel family, is considered to cause the foregoing ionic current.

These reports have revealed that menthol binds to TRPM8 present in the sensory nerve to generate an inward current, and consequently the cooling sensation due to menthol arises.

CITATION LIST

Non Patent Literature

[Non Patent Literature 1] REID, G. & FLONTA, M. L. (2002), Neurosci. Lett., 324, p 164-168
[Non Patent Literature 2] MCKEMY, D. D., NEUHAUSSER, W. M. & JULIUS, D. (2002), Nature, 416, p 52-56
[Non Patent Literature 3] PEIER, A. M., MOQRICH, A., HERGARDEN, A. C., REEVE, A. J., ANDERSSON, D. A., STORY, G. M., EARLEY, T. J., DRAGONI, I., MCINTYRE, P., BEVAN, S. & PATAPOUTIAN, A. (2002), Cell, 108, p 705-715
[Non Patent Literature 4] BEHRENDT, H.-J., GERMANN, T., GILLEN, C., HATT, H. & JOSTOCK, R. (2004), Br. J. Pharmacol., 141, p 737-745

SUMMARY OF THE INVENTION

The present invention provides a method for producing a processed nutmeg product, comprising a step of simultaneously treating nutmeg or an extract thereof with an alcohol or a 25% (v/v) or more alcohol aqueous solution and one or more selected from a protonic acid and an H-type cation exchange resin.

The present invention also provides a processed nutmeg product obtained by the foregoing production method.

The present invention further provides a cooling agent comprising, as an active ingredient, the processed nutmeg product.

The present invention further provides a TRPM8 activator comprising, as an active ingredient, the processed nutmeg product.

The present invention further provides a cosmetic comprising the processed nutmeg product.

The present invention further provides an oral composition comprising the processed nutmeg product.

The present invention provides a cooling agent comprising, as an active ingredient, a distillation residue of a nutmeg extract.

The present invention further provides a TRPM8 activator comprising, as an active ingredient, a distillation residue of a nutmeg extract.

The present invention further provides a cosmetic comprising a distillation residue of a nutmeg extract.

The present invention further provides an oral composition comprising a distillation residue of a nutmeg extract.

BRIEF DESCRIPTION OF DRAWING

FIG. 1 is a graph showing the cooling sensation of the mouthwash of Example 1-13.

DESCRIPTION OF EMBODIMENTS

The present invention relates to a processed plant product having an excellent TRPM8 activating action, a method for producing the same, and a cooling agent using the processed plant product and a TRPM8 activator obtained by using the processed plant product.

The present invention also relates to a cooling agent, a TRPM8 activator, a cosmetic and an oral composition having an excellent TRPM8 activating action.

The use of menthol in a large amount sometimes causes a problem such as an irritation against the skin or the mucous membrane, or a specific unpleasant irritating odor, and accordingly the amount used thereof is sometimes limited.

In addition to menthol, for example, linalool, geraniol and hydroxycitronellal are known to activate TRPM8 (Non Patent Literature 4); however, the refreshing feeling offered by the compound described in Non Patent Literature 4 has been not necessarily sufficient.

The present inventors perfected the present invention by discovering that a processed nutmeg product having an excellent TRPM8 activating action is obtained by simultaneously treating nutmeg or an extract thereof with an alcohol or a 25% (v/v) or more alcohol aqueous solution and one or more selected from a protonic acid and an H-type cation exchange resin.

The present inventors also perfected the present invention by discovering that a distillation residue of a nutmeg extract has an excellent TRPM8 activating action.

According to the method for producing a processed nutmeg product of the present invention, a processed nutmeg product having an excellent TRPM8 activating action can be produced.

The processed nutmeg product of the present invention has an excellent TRPM8 activating action, and by using the processed nutmeg product, a satisfactory cooling sensation can be imparted.

The cooling agent and the TRPM8 activator each comprising, as an active ingredient, the distillation residue of the nutmeg extract of the present invention each have an excellent TRPM8 activating action, and by using the cooling agent or the TRPM8 activator, a satisfactory cooling sensation can be imparted.

<Method for Producing Processed Nutmeg Product>

The method for producing a processed nutmeg product of the present invention comprises a step of simultaneously treating nutmeg or an extract thereof with an alcohol or a 25% (v/v) or more alcohol aqueous solution and one or more selected from a protonic acid and an H-type cation exchange resin (hereinafter, the processed nutmeg product obtained by the production method of the present invention is also simply referred to as the processed nutmeg product).

The above-mentioned nutmeg means *Myristica fragrans* Houtt., which is a plant belonging to the Myristicaceae. As nutmeg, the seeds, mace, leaves, fruits and the like thereof are used, and the seeds or the mace is preferable from the viewpoint of the TRPM8 activating action. These parts may be used each alone or in combinations of two or more thereof.

Nutmeg can be used as it is, or one prepared by drying nutmeg and subsequently cutting or crushing the dried nutmeg to an appropriate size can be used.

In the present invention, extraction of nutmeg can be performed by using, for example, the following methods: a method in which nutmeg is soaked in a solvent at room temperature or at a heating temperature, a solvent extraction method performed by using an extraction apparatus such as a Soxhlet extractor, a supercritical extraction method performed by using carbon dioxide gas or the like in a supercritical state, and a compression method in which an extract is obtained by compression. Alternatively, extraction may be performed again by using a solvent or the like from the residue obtained by, for example, steam distillation or microwave steam distillation.

Distillation may also be performed after the extraction with the foregoing methods; however, in this case, it is preferable to use the distillation residue from the viewpoint of the TRPM8 activating action. The distillation method may be a heretofore known method such as a molecular distillation, a steam distillation or a microwave distillation. Such a distillation operation can be performed under normal pressure or reduced pressure, and the distillation temperature is usually from 30 to 150° C., preferably from 60 to 130° C.

When an extraction solvent is used in the extraction, as the extraction solvent, any of a polar solvent and a non-polar solvent may be used. Examples of such a solvent include: water; alcohols (for examples, the alcohols used in the below-described treatment) such as methanol, ethanol, propanol, butanol and cyclohexanol; polyhydric alcohols such as propylene glycol and butylene glycol; ketones such as acetone and methyl ethyl ketone; esters such as methyl acetate and ethyl acetate; chain or cyclic ethers such as diethyl ether and tetrahydrofuran; polyethers such as polyethylene glycol; hydrocarbons such as squalane, hexane and cyclohexane; aromatic hydrocarbons such as benzene and toluene; halogenated hydrocarbons such as dichloromethane, chloroform and dichloroethane; and additionally, supercritical carbon dioxide, fats, waxes oils and the like. These may be used each alone or in combinations of two or more thereof.

Among these, a liquid mixture composed of water and a polar solvent and a polar solvent are preferable, and a water-alcohol liquid mixture and alcohols are more preferable. As described below, a protonic acid or the like may be included in the extraction solvent.

When the liquid mixture composed of water and a polar solvent is used, the concentration of the polar solvent is preferably 25% (v/v) or more, more preferably 35% (v/v) or more, even more preferably 50% (v/v) or more, even more preferably 70% (v/v) or more, even more preferably 80% (v/v) or more, even more preferably 90% (v/v) or more, and preferably 99.9% (v/v) or less. Specifically, the concentration of the polar solvent in the liquid mixture is preferably from 25 to 99.9% (v/v), more preferably from 35 to 99.9% (v/v), even more preferably from 50 to 99.9% (v/v), even more preferably from 70 to 99.9% (v/v), even more preferably from 80 to 99.9% (v/v), even more preferably from 90 to 99.9% (v/v).

The amount of the extraction solvent used is not particularly limited, but is, in relation to 1 part by mass of nutmeg, usually 1 part by mass or more, preferably 3 parts by mass or more, more preferably 5 parts by mass or more, and usually 50 parts by mass or less, preferably 30 parts by mass or less, more preferably 25 parts by mass or less, even more preferably 15 parts by mass or less. Specifically, the amount of the extraction solvent used is, in relation to 1 part by mass of nutmeg, preferably from 1 to 50 parts by mass, more preferably from 3 to 30 parts by mass, even more preferably from 5 to 25 parts by mass.

The extraction temperature is usually 3° C. or higher, preferably 10° C. or higher, more preferably 20° C. or higher, and usually 100° C. or lower, preferably 60° C. or lower, more preferably 45° C. or lower. Specifically, the extraction temperature is preferably from 3 to 100° C., more preferably from 10 to 60° C., even more preferably from 20 to 45° C.

The extraction time is usually 1 hour or more and usually 14 days or less, preferably 7 days or less, more preferably 5 days or less. Specifically, the extraction time is preferably from 1 hour to 14 days, more preferably from 1 hour to 7 days, even more preferably from 1 hour to 5 days.

As for the pressure at the time of extraction, the extraction is usually performed under normal pressure, but can also be performed under a high pressure.

The method for producing a processed nutmeg product of the present invention is a method comprising simultaneously treating nutmeg or an extract thereof (hereinafter, nutmeg or an extract thereof is also referred to as nutmeg or the like) with an alcohol or a 25% (v/v) or more alcohol aqueous solution (hereinafter, an alcohol or a 25% (v/v) or more alcohol aqueous solution is also referred to as an alcohol or the like) and one or more selected from a protonic acid and an H-type cation exchange resin (hereinafter, one or more selected from a protonic acid and an H-type cation exchange resin are also referred to as a protonic acid or the like); this means that nutmeg or the like, an alcohol or the like and a protonic acid or the like are made to be concomitantly present, and the order of the addition of the individual components is not particularly specified. Such a treatment as described above may be performed as the extraction of nutmeg or may also be performed after the extraction of nutmeg.

Specific examples of the treatment include: (1) a method in which the extraction is performed by using an extraction solvent including an alcohol or the like and a protonic acid or the like; (2) a method in which the extraction is performed by using an extraction solvent including an alcohol or the like but not including a protonic acid or the like, and subsequently the resulting extract is treated with a protonic acid or the like; and (3) a method in which a nutmeg extract obtained by the extraction using an appropriate extraction solvent is simultaneously treated with an alcohol or the like and a protonic acid or the like wherein the alcohol or the like and the protonic acid or the like are made, for example, to be concomitantly present.

In the method (1), the obtained nutmeg extract may be distilled, and the resulting distillation residue may be adopted as a processed nutmeg product. In the method (3), the nutmeg extract obtained by the extraction using an appropriate extraction solvent may be further distilled, and the resulting distillation residue may be simultaneously treated with an alcohol or the like and a protonic acid or the like.

For the treatment included in the method for producing a processed nutmeg product of the present invention, an alcohol or a 25% (v/v) or more alcohol aqueous solution is used. As the alcohol used for such a treatment, a monohydric alcohol is preferable. The number of the carbon atoms in the monohydric alcohol is preferably from 1 to 10, more preferably from 1 to 6, even more preferably from 2 to 6 from the viewpoint of the TRPM8 activating action. Examples of such a monohydric alcohol include methanol, ethanol, propanol, butanol and cyclohexanol; these may be used each alone or in combinations of two or more thereof.

The concentration of the alcohol aqueous solution is preferably 35% (v/v) or more, more preferably 50% (v/v) or more, even more preferably 70% (v/v) or more, even more preferably 80% (v/v) or more, even more preferably 90% (v/v) or more, and preferably 99.9% (v/v) or less from the viewpoint of the TRPM8 activating action. Specifically, the concentration of the alcohol aqueous solution is preferably from 35 to 99.9% (v/v), more preferably from 50 to 99.9% (v/v), even more preferably from 70 to 99.9% (v/v), even more preferably from 80 to 99.9% (v/v), even more preferably from 90 to 99.9% (v/v). In the case where the alcohol aqueous solution is used, when the concentration of the alcohol aqueous solution is less than 25% (v/v), the TRPM8 activating action of the processed nutmeg product comes to be insufficient.

The amount of the alcohol or the like used is not particularly limited; however, the amount of the alcohol or the like used is, in relation to 1 part by mass of the nutmeg or the like, usually 0.1 part by mass or more, preferably 1 part by mass or more, more preferably 2 parts by mass or more, and usually 1000 parts by mass or less, preferably 500 parts by mass or less, more preferably 200 parts by mass or less. Specifically, the amount of the alcohol or the like used is, in relation to 1 part by mass of nutmeg or the like, preferably from 0.1 to 1000 parts by mass, more preferably from 1 to 500 parts by mass, even more preferably from 2 to 200 parts by mass.

For the treatment, one or more selected from a protonic acid and an H-type cation exchange resin are used. Examples of the protonic acid used in such a treatment include organic acids and inorganic acids. These may be used each alone or in combinations of two or more thereof.

Examples of the organic acids include citric acid, acetic acid and paratoluenesulfonic acid.

Examples of the inorganic acids include sulfuric acid, hydrochloric acid, nitric acid and phosphoric acid.

Examples of the H-type cation exchange resin include AMBERLYST (Dow Chemical Co.), DOWEX (manufactured by Dow Chemical Co.), DIAION (manufactured by Mitsubishi Chemical Corp.). The treatment with the H-type cation exchange resin may be performed by adding the H-type cation exchange resin or by passing through a column packed with the H-type cation exchange resin.

Among the foregoing protonic acids and the foregoing H-type cation exchange resins, from the viewpoint of the TRPM8 activating action, a strongly acidic protonic acid and a strongly acidic H-type cation exchange resin are preferable.

The amount of the protonic acid or the like used is not particularly limited; however, the amount of the protonic acid or the like used is, in relation to 1 part by mass of the nutmeg or the like, usually 0.001 part by mass or more, preferably 0.01 part by mass or more, and usually 50 parts by mass or less, preferably 25 parts by mass or less, more preferably 10 parts by mass or less, even more preferably 5 parts by mass or less. Specifically, the amount of the protonic acid or the like used is, in relation to 1 part by mass of the nutmeg or the like, preferably from 0.01 to 50 parts by mass, more preferably from 0.01 to 10 parts by mass, even more preferably from 0.01 to 5 parts by mass.

The treatment temperature is usually 3° C. or higher, preferably 15° C. or higher, more preferably 25° C. or higher, and usually 100° C. or lower, preferably 70° C. or lower, more preferably 60° C. or lower. Specifically, the treatment temperature is preferably from 3 to 100° C., more preferably from 15 to 70° C., even more preferably from 25 to 60° C.

The treatment time is usually 0.1 hour or more, preferably 1 hour or more, more preferably 2 hours or more, and usually 5 days or less, preferably 3 days or less, more preferably 2 days or less. Specifically, the treatment time is from 0.1 hour to 5 days, more preferably from 1 hour to 3 days, even more preferably from 2 hours to 2 days.

The obtained processed nutmeg product is, for example, diluted, concentrated or freeze-dried, and then, if necessary, prepared into a powder form or a paste form and thus-prepared one can be used.

Examples of the solvent used for diluting the processed nutmeg product include the alcohols and water used in the foregoing treatment and the liquid mixtures of these. Examples of means for the concentration or purification of the processed nutmeg product include the filtration, the activated carbon treatment and the liquid-liquid partition of the processed product.

The processed nutmeg product of the present invention has, as shown in below-described Examples, an excellent TRPM8 activating action in spite of being originated from a natural product.

Accordingly, the processed nutmeg product of the present invention can be used as a cooling agent and a TRPM8 activator, as it is or in combination with, for example, various formulation carriers or various preservatives.

<Cooling Agent or TRPM8 Activator Comprising, as Active Ingredient, Distillation Residue of Nutmeg Extract>

Next, a cooling agent or a TRPM8 activator comprising, as an active ingredient, the distillation residue of the nutmeg extract of the present invention is described.

The above-mentioned nutmeg means *Myristica fragrans* Houtt., which is a plant belonging to the Myristicaceae. As nutmeg, the seeds, mace, leaves, and fruits thereof are used, and from the viewpoint of the TRPM8 activating action, the seeds or the mace is preferable. The nutmeg extract may be a product obtained by using these parts each alone or in combinations of two or more thereof. The nutmeg extract may also be a product obtained by extracting nutmeg as it is, or one obtained by drying nutmeg and subsequently cutting or crushing the dried nutmeg to an appropriate size, followed by extraction.

As the nutmeg extract, a commercially available product may be used; and, one prepared by extracting nutmeg according to a routine procedure may also be used. Such an extraction can be performed by, for example, a method in which nutmeg is soaked in a solvent at room temperature or at a heating temperature, a solvent extraction method in which extraction is performed by using an extraction apparatus such as a Soxhlet extractor, a supercritical extraction method in which extraction is performed by using, for example, carbon dioxide gas in a supercritical state, or a compression method in which an extract is obtained by compression. Alternatively, from the residue obtained by performing steam distillation or microwave steam distillation, extraction may also be performed again by using, for example, a solvent.

Among the foregoing extraction methods, when an extract to be used for the distillation residue is obtained, the supercritical extraction method is preferable from the viewpoint of the TRPM8 activating action. The supercritical extraction method is a method in which a supercritical fluid is brought into contact with nutmeg, and examples of the supercritical extraction method include a method in which a substance such as carbon dioxide is allowed to be in a supercritical state (a supercritical fluid), and the substance in a supercritical state is brought into contact with nutmeg in a condition capable of performing the extraction, to thereby perform the extraction.

When an extraction solvent is used in the extraction, as the extraction solvent, any of a polar solvent and a non-polar solvent may be used. Examples of such a solvent include: water; alcohols such as methanol, ethanol, propanol, butanol and cyclohexanol; polyhydric alcohols such as propylene glycol and butylene glycol; ketones such as acetone and methyl ethyl ketone; esters such as methyl acetate and ethyl acetate; chain or cyclic ethers such as diethyl ether and tetrahydrofuran; polyethers such as polyethylene glycol; hydrocarbons such as squalane, hexane and cyclohexane; aromatic hydrocarbons such as benzene and toluene; halogenated hydrocarbons such as dichloromethane, chloroform and dichloroethane; and additionally, supercritical carbon dioxide, fats, waxes, oils and the like. These may be used each alone or in combinations of two or more thereof.

Among these, when an extract to be used for the distillation residue is obtained, from the viewpoint of the TRPM8 activating action, a liquid mixture of water and a polar solvent, polar solvents and supercritical carbon dioxide are preferable, a water-alcohol liquid mixture, alcohols and supercritical carbon dioxide are more preferable, and supercritical carbon dioxide is even more preferable.

When the liquid mixture composed of water and a polar solvent is used, the concentration of the polar solvent is preferably 25% (v/v) or more, more preferably 35% (v/v) or more, even more preferably 50% (v/v) or more, even more preferably 70% (v/v) or more, even more preferably 80% (v/v) or more, even more preferably 90% (v/v) or more, and preferably 99.9% (v/v) or less. Specifically, the concentration of the polar solvent in the liquid mixture is preferably from 25 to 99.9% (v/v), more preferably from 35 to 99.9% (v/v), even more preferably from 50 to 99.9% (v/v), even more preferably from 70 to 99.9% (v/v), even more preferably from 80 to 99.9% (v/v), even more preferably from 90 to 99.9% (v/v).

The amount of the extraction solvent used is not particularly limited, but is, in relation to 1 part by mass of nutmeg, usually 1 part by mass or more, preferably 3 parts by mass or more, more preferably 5 parts by mass or more, and usually 50 parts by mass or less, preferably 30 parts by mass or less, more preferably 25 parts by mass or less, even more preferably 15 parts by mass or less. Specifically, the amount of the extraction solvent used is, in relation to 1 part by mass of nutmeg, preferably from 1 to 50 parts by mass, more preferably from 3 to 30 parts by mass, even more preferably from 5 to 25 parts by mass.

The extraction temperature is usually 3° C. or higher, preferably 10° C. or higher, more preferably 20° C. or higher, and usually 100° C. or lower, preferably 60° C. or lower, more preferably 45° C. or lower. Specifically, the extraction temperature is preferably from 3 to 100° C., more preferably from 10 to 60° C., even more preferably from 20 to 45° C.

The extraction time is usually 1 hour or more, and usually 14 days or less, preferably 7 days or less, more preferably 5 days or less. Specifically, the extraction time is preferably from 1 hour to 14 days, more preferably from 1 hour to 7 days, even more preferably from 1 hour to 5 days.

As for the pressure at the time of extraction, the extraction is usually performed under normal pressure, but can also be performed under a high pressure.

The distillation of the extract obtained as described above may be performed by a heretofore known method such as a molecular distillation, a steam distillation or a microwave distillation, and the conditions, the number of stages and the apparatus of the distillation are not particularly limited.

Such a distillation operation can be performed under normal pressure or reduced pressure, and the distillation pressure is preferably 0.05 Pa or more, more preferably 0.1 Pa or more, and preferably 1000 Pa or less, more preferably 200 Pa or less, even more preferably 30 Pa or less. Specifically, the distillation pressure is preferably from 0.05 to 1000 Pa, more preferably from 0.1 to 200 Pa, even more preferably from 0.1 to 30 Pa.

The distillation temperature is preferably 30° C. or higher, more preferably 45° C. or higher, even more preferably 60° C. or higher, and preferably 150° C. or lower, more preferably 140° C. or lower, even more preferably 130° C. or lower. Specifically, the distillation temperature is preferably from 30 to 150° C., more preferably from 45 to 140° C., even more preferably from 60 to 130° C.

The residue obtained by further distilling one or more times (preferably from 1 to 3 times) the distillation residue of the nutmeg extract obtained as described above may also be used as the distillation residue. The use of such a distillation residue improves the TRPM8 activating action.

The obtained distillation residue is, for example, diluted, concentrated or freeze-dried, and then, if necessary, prepared into a powder form or a paste form and thus-prepared one can be used.

Examples of the solvent used for diluting the distillation residue include alcohols, water and the liquid mixtures composed of these. Examples of the means for the concentration or purification of the distillation residue include the filtration, the activated carbon treatment and the liquid-liquid partition of the distillation residue.

As shown in below-described Examples, the distillation residue of the nutmeg extract has an excellent TRPM8 activating action in spite of being originated from a natural product and being obtainable by an extremely simple operation. In the present invention, the distillation residue means a substance remaining undistilled when the nutmeg extract is distilled.

Accordingly, the distillation residue of the nutmeg extract can be used as a cooling agent and a TRPM8 activator as it is or in combination with, for example, various formulation carriers or various preservatives.

Next, the modes of the cooling agent and the TRPM8 activator (hereinafter, also referred to as the cooling agent and the like) each comprising, as the active ingredient, the processed nutmeg product or the distillation residue.

The cooling agent and the like may be themselves pharmaceuticals for human or animals, cosmetics, food and drink, oral compositions, pet food and other luxury grocery items (such as tobacco), or alternatively, may be cooling sensation-imparting materials to be added to, for example, these pharmaceuticals.

The pharmaceuticals can be administered in optional administration forms. The administration forms are generally classified into the parenteral administration such as transmucosal administration or transdermal administration and the oral administration.

The dosage forms of the pharmaceuticals are not particularly limited. Examples of the dosage forms of the pharmaceuticals for parenteral administration include: skin preparations for external use such as liquids, gels, creams, ointments, cataplasms, aerosols, lotions and foundations; and additionally, eye drops and nasal drops.

On the other hand, examples of the dosage forms of the pharmaceuticals for oral administration include: tablets, capsules, granules, pulvis, powders, pills, sugar-coated tablets, internal liquids, suspensions and syrups.

The pharmaceuticals may include other medicinal ingredients such as an anti-inflammatory analgesic, a sterilizing disinfectant, an astringent and an antibiotic. These may be used each alone or in combinations of two or more thereof.

The forms of the cosmetics, food and drink and oral compositions are not particularly limited.

Cosmetics may be, for example, skin preparation for external use (such as insect repellent spray), cleaners, lotions, milky lotions, skin creams, foundations, lipsticks, scalp cosmetics, hair cosmetics (such as shampoo and hair tonic), bath additive and sheet products. Cosmetics may also include, in addition to the processed nutmeg product or the distillation residue of the nutmeg extract, for example, oil solutions, ceramides, pseudo-ceramides, sterols, humectants, antioxidants, ultraviolet absorbers, whitening agents, alcohols, chelating agents, pH adjusters and antiseptics. These may be used each alone or in combinations of two or more thereof.

Examples of food and drink include candies, gums, tablets, capsules and drinking water.

Examples of the oral compositions include dentifrices, mouthwashes and gingiva massage creams.

The content of the processed nutmeg product or the distillation residue of the nutmeg extract is not particularly limited; however, in the cases of the pharmaceuticals for oral administration, food and drink, oral compositions or pet food, from the viewpoint of the TRPM8 activating action, the content of the processed nutmeg product or the distillation residue of the nutmeg extract is preferably 0.1 ppm or more, more preferably 1 ppm or more, even more preferably 10 ppm or more, even more preferably 50 ppm or more, and preferably 10000 ppm or less, more preferably 5000 ppm or less, even more preferably 2500 ppm or less, even more preferably 1000 ppm or less.

Specifically, in such cases as described above, from the viewpoint of the TRPM8 activating action, the content of the processed nutmeg product or the distillation residue of the nutmeg extract is preferably from 0.1 to 10000 ppm, more preferably from 1 to 10000 ppm, even more preferably from 10 to 5000 ppm, even more preferably from 50 to 2500 ppm.

In the cases of the pharmaceuticals for parenteral administration, cosmetics or other luxury grocery items, from the viewpoint of the TRPM8 activating action, the content of the processed nutmeg product or the distillation residue of the nutmeg extract is preferably 0.001% by mass or more, more preferably 0.01% by mass or more, and preferably 10% by mass or less. Specifically, in such cases as described above, from the viewpoint of the TRPM8 activating action, the content of the processed nutmeg product or the distillation residue of the nutmeg extract is preferably from 0.001 to 10% by mass, more preferably from 0.01 to 10% by mass.

In relation to the foregoing embodiment, the present invention further discloses the following production methods and the like.

<1> A method for producing a processed nutmeg product, the method comprising a step of simultaneously treating nutmeg or an extract thereof with an alcohol or a 25% (v/v) or more alcohol aqueous solution and one or more selected from a protonic acid and an H-type cation exchange resin.

<2> A method for producing a processed nutmeg product, comprising a step of extracting nutmeg by using an extraction solvent comprising an alcohol or a 25% (v/v) or more alcohol aqueous solution and one or more selected from a protonic acid and an H-type cation exchange resin.

<3> A method for producing a processed nutmeg product, comprising steps of extracting nutmeg using an extraction solvent comprising an alcohol or a 25% (v/v) or more alcohol aqueous solution but not comprising one or more selected from a protonic acid and an H-type cation exchange resin, and treating the obtained extract with one or more selected from the protonic acid and the H-type cation exchange resin.

<4> A method for producing a processed nutmeg product, comprising steps of extracting nutmeg by using an extraction solvent, and treating the obtained extract with an alcohol or a 25% (v/v) or more alcohol aqueous solution and one or more selected from a protonic acid and an H-type cation exchange resin.

<5> The production method according to any one of the foregoing <1> to <4>, wherein as the alcohol, preferably an alcohol having 1 to 10 carbon atoms, more preferably an alcohol having 1 to 6 carbon atoms, even more preferably an alcohol having 2 to 6 carbon atoms is used.

<6> The production method according to any one of the foregoing <1> to <5>, wherein the concentration of the alcohol aqueous solution is preferably 35% (v/v) or more, more preferably 50% (v/v) or more, even more preferably 70% (v/v) or more, even more preferably 80% (v/v) or more, even more preferably 90% (v/v) or more, and preferably 99.9% (v/v) or less.

<7> The production method according to any one of the foregoing <1> to <6>, wherein the amount of the alcohol or the 25% (v/v) or more alcohol aqueous solution used is, in relation to 1 part by mass of nutmeg or the extract thereof, preferably 0.1 part by mass or more, more preferably 1 part by mass or more, even more preferably 2 parts by mass or more, and preferably 1000 parts by mass or less, more preferably 500 parts by mass or less, even more preferably 200 parts by mass or less.

<8> The production method according to any one of the foregoing <1> to <7>, wherein as the protonic acid, one or more selected from an organic acid and an inorganic acid are used.

<9> The production method according to any one of the foregoing <1> to <8>, wherein one or more selected from a strongly acidic protonic acid and a strongly acidic H-type cation exchange resin are used.

<10> The production method according to any one of the foregoing <1> to <9>, wherein the amount of one or more selected from the protonic acid and the H-type cation exchange resin used is, in relation to 1 part by mass of nutmeg or the extract thereof, preferably 0.001 part by mass or more, more preferably 0.01 part by mass or more, and preferably 50 parts by mass or less, more preferably 25 parts by mass or less, even more preferably 10 parts by mass or less.

<11> The production method according to any one of the foregoing <1> to <10>, wherein the treatment temperature is preferably 3° C. or higher, more preferably 15° C. or higher, even more preferably 25° C. or higher, and preferably 100° C. or lower, more preferably 70° C. or lower, even more preferably 60° C. or lower.

<12> The production method according to any one of the foregoing <1> to <11>, wherein the treatment time is preferably 0.1 hour or more, more preferably 1 hour or more, even more preferably 2 hours or more, and preferably 5 days or less, more preferably 3 days or less, even more preferably 2 days or less.

<13> A processed nutmeg product obtained by the production method according to any one of the foregoing <1> to <12>.

<14> A cooling agent comprising, as an active ingredient, the processed nutmeg product according to the foregoing <13>.

<15> A TRPM8 activator comprising, as an active ingredient, the processed nutmeg product according to the foregoing <13>.

<16> A cosmetic comprising the processed nutmeg product according to the foregoing <13>.

<17> An oral composition comprising the processed nutmeg product according to the foregoing <13>.

<18> A cooling agent comprising, as an active ingredient, a distillation residue of a nutmeg extract.

<19> A TRPM8 activator comprising, as an active ingredient, a distillation residue of a nutmeg extract.

<20> A cosmetic comprising a distillation residue of a nutmeg extract.

<21> An oral composition comprising a distillation residue of a nutmeg extract.

<22> The cooling agent, the TRPM8 activator, the cosmetic or the oral composition according to any one of the foregoing <18> to <21>, wherein the nutmeg extract is a nutmeg extract extracted by a supercritical extraction method.

<23> The cooling agent, the TRPM8 activator, the cosmetic or the oral composition according to any one of the foregoing <18> to <22>, wherein the nutmeg extract is preferably an extract extracted by using a solvent selected from a liquid mixture composed of water and a polar solvent, a polar solvent and supercritical carbon dioxide, more preferably an extract extracted by using a solvent selected from a water-alcohol liquid mixture, an alcohol and supercritical carbon dioxide, even more preferably an extract extracted by using supercritical carbon dioxide.

<24> The cooling agent, the TRPM8 activator, the cosmetic or the oral composition according to the foregoing <23>, wherein the concentration of the liquid mixture is preferably 25% (v/v) or more, more preferably 35% (v/v) or more, even more preferably 50% (v/v) or more, even more preferably 70% (v/v) or more, even more preferably 80% (v/v) or more, even more preferably 90% (v/v) or more, and preferably 99.9% (v/v) or less.

<25> The cooling agent, the TRPM8 activator, the cosmetic or the oral composition according to any one of the foregoing <18> to <24>, wherein the distillation residue is a residue obtained by distilling the nutmeg extract under a pressure of preferably 0.05 Pa or more, more preferably 0.1 Pa or more, and preferably 1000 Pa or less, more preferably 200 Pa or less, even more preferably 30 Pa or less.

<26> The cooling agent, the TRPM8 activator, the cosmetic or the oral composition according to any one of foregoing <18> to <25>, wherein the distillation residue is a residue obtained by distilling the nutmeg extract at a temperature of preferably 30° C. or higher, more preferably 45° C. or higher, even more preferably 60° C. or higher, and preferably 150° C. or lower, more preferably 140° C. or lower, even more preferably 130° C. or lower.

<27> The cooing agent, the TRPM8 activator, the cosmetic or the oral composition according to any one of foregoing <18> to <26>, wherein the distillation residue is a residue obtained by further distilling the distillation residue of the nutmeg extract one or more times.

EXAMPLES

Hereinafter, the present invention is described in detail with reference to Examples, but the present invention is not limited to these Examples.

Preparation Example 1: Extract Treated with Ethanol

To 5 g of seeds of nutmeg (*Myristica fragrans* Houtt., Myristicaceae), 50 mL of 99.5 vol % ethanol was added, the seeds were soaked and extracted at room temperature for 2 days, and then the seeds were filtered out to yield a crude extract (a product untreated with an acid). The evaporation residue of the obtained crude extract was 1.05 w/v %.

Example 1-1: Extract Treated with Ethanol and Hydrochloric Acid

To 5 mL of the crude extract (solid content: 52.5 mg) obtained in Preparation Example 1, hydrochloric acid (1.1M aqueous solution, 0.05 mL) was added and mixed so that the whole resulting mixture became uniform, and the mixture was allowed to stand still at 60° C. for 2 days to yield an extract treated with ethanol and hydrochloric acid (evaporation residue: 1.05 w/v %).

Example 1-2: Extract Treated with Ethanol and Strongly Acidic Cation Exchange Resin To 5 mL of the crude extract (solid content: 52.5 mg) obtained in Preparation Example 1, 52.5 mg of a strongly acidic cation exchange resin (AMBERLYST 15JW, manufactured by Dow Chemical Co.) was added and stirred, and then the resulting mixture was allowed to stand still at 60° C. for 2 days. The resin in the extract was filtered out to yield, as a filtrate, an extract treated with ethanol and the strongly acidic cation exchange resin (evaporation residue: 1.05 w/v %).

Example 1-3: Extract Treated with Ethanol and Citric Acid

To 5 mL of the crude extract (solid content: 52.5 mg) obtained in Preparation Example 1, citric acid (960 mg) was added and stirred, and then the resulting mixture was allowed to stand still at 60° C. for 2 days. Subsequently, the ethanol was removed by nitrogen flow, and then to the mixture, hexane (2.5 mL) and a saturated sodium hydrogen carbonate aqueous solution (2.5 mL) were added. From the resulting mixture, the water phase thereof was discarded, and then the hexane phase thereof was concentrated and dissolved again in ethanol (5 mL) to yield an extract treated with ethanol and citric acid (evaporation residue: 0.60 w/v %).

Example 1-4: Extract Treated with n-Butanol and Hydrochloric Acid

After 5 mL of the crude extract (solid content: 52.5 mg) obtained in Preparation Example 1 was concentrated, the resulting concentrate was dissolved in n-butanol (5 mL), and to the resulting solution, hydrochloric acid (1.1M aqueous solution, 0.05 mL) was added. The solution was stirred, and then allowed to stand still at 60° C. for 2 days to yield an extract treated with n-butanol and hydrochloric acid (evaporation residue: 0.85 w/v %).

Example 1-5: Extract Treated with n-Butanol and Strongly Acidic Cation Exchange Resin After 5 mL of the crude extract (solid content: 52.5 mg) obtained in Preparation Example 1 was concentrated, the resulting concentrate was dissolved in n-butanol (5 mL), to the resulting solution, 52.5 mg of a strongly acidic cation exchange resin (AMBERLYST 15JW, manufactured by Dow Chemical Co.) was added and stirred, and then the resulting mixture was allowed to stand still at 60° C. for 2 days. The resin in the extract was filtered out to yield, as a filtrate, an extract treated with n-butanol and the strongly acidic cation exchange resin (evaporation residue: 0.78 w/v %).

Example 1-6: Extract Treated with Ethanol and Strongly Acidic Cation Exchange Resin To 8 g of mace of nutmeg (*Myristica fragrans* Houtt., Myristicaceae), 80 mL of 99.5 vol % ethanol was added, the mace was soaked and extracted at room temperature for 1 day, and then the mace was filtered out to yield a crude extract (evaporation residue: 1.17 w/v %). To the crude extract, 936 mg of a strongly acidic cation exchange resin (AMBERLYST 15JW, manufactured by Dow Chemical Co.) was added and stirred, and then the resulting mixture was allowed to stand still at 60° C. for 2 days. The resin in the extract was filtered out to yield, as a filtrate, an extract treated with ethanol and the strongly acidic cation exchange resin (evaporation residue: 1.17 w/v %).

Example 1-7: Extract Treated with Ethanol and Strongly Acidic Cation Exchange Resin To 20 g of leaves of nutmeg (*Myristica fragrans* Houtt., Myristicaceae), 400 mL of 99.5 vol % ethanol was added, the leaves were soaked and extracted at room temperature for 4 days, and then the leaves were filtered out to yield a crude extract (evaporation residue: 0.32 w/v %). To the crude extract, 640 mg of a strongly acidic cation exchange resin (AMBERLYST 15JW, manufactured by Dow Chemical Co.) was added and stirred, and then the resulting mixture was allowed to stand still at 60° C. for 2 days. The resin in the extract was filtered out to yield, as a filtrate, an extract treated with ethanol and the strongly acidic cation exchange resin (evaporation residue: 0.32 w/v %).

Example 1-8: Product Treated with Ethanol and Strongly Acidic Cation Exchange Resin In the same manner as in Preparation Example 1, to 10 g of seeds of nutmeg (*Myristica fragrans* Houtt., Myristicaceae), 100 mL of 99.5 vol % ethanol was added, the seeds were soaked and extracted at room temperature for 2 days, and then the seeds were filtered out to yield a crude extract (evaporation residue: 1.05 w/v %). The resulting solution was made to pass through a column packed with 5 g of a strongly acidic cation exchange resin (AMBERLYST 15JW, manufactured by Dow Chemical Co.) at 50° C. for 2 days to yield an extract treated with ethanol and the strongly acidic cation exchange resin.

Next, the extract was added with water and concentrated, and the resultant concentrate was then dissolved again in 100 mL of ethanol. To the resulting solution, activated carbon was added, and the resulting mixture was allowed to stand still at room temperature for 2 days, and then the activated carbon was filtered out. Next, the resulting filtrate was concentrated under reduced pressure to yield a nutmeg extract treated with ethanol and the strongly acidic cation exchange resin (141 mg).

Comparative Example 1: Extract Treated with DMSO and Hydrochloric Acid

After 5 mL of the crude extract (solid content: 52.5 mg) obtained in Preparation Example 1 was concentrated to remove the ethanol, the resulting concentrate was dissolved in DMSO (5 mL), and hydrochloric acid (1.1M aqueous solution, 0.05 mL) was added to the solution. After the solution was stirred, the solution was allowed to stand still at 60° C. for 2 days to yield an extract treated with DMSO and hydrochloric acid (evaporation residue: 1.05 w/v %).

Preparation Example 2: Product Treated with Ethanol

In the same manner as in Preparation Example 1, to 10 g of seeds of nutmeg (*Myristica fragrans* Houtt., Myristicaceae), 100 mL of 99.5 vol % ethanol was added, the seeds were soaked and extracted at room temperature for 2 days, and then the seeds were filtered out to yield a crude extract (evaporation residue: 1.05 w/v %). The resulting extract was concentrated by adding water to yield a nutmeg extract treated with ethanol (835 mg).

Example 1-9: Extract Treated with Ethanol and Strongly Acidic Cation Exchange Resin In ethanol (5 mL), 50.0 mg of a supercritical carbon dioxide extract of seeds of nutmeg (*Myristica fragrans* Houtt., Myristicaceae) (purchased from PT MITRA AYU ADIPRATAMA) was dissolved. To the resulting solution, 50 mg of a strongly acidic cation exchange resin (AMBERLYST 15JW, manufactured by Dow Chemical Co.) was added and stirred, and then the resulting mixture was allowed to stand still at 60° C. for 1 day. The resin in the extract was filtered out to yield, as a filtrate, an extract treated with ethanol and the strongly acidic cation exchange resin (evaporation residue: 1.00 w/v %).

Example 1-10: Extract Treated with 50% Ethanol Aqueous Solution and Strongly Acidic Cation Exchange Resin In a 50% ethanol aqueous solution (5 mL), 50.0 mg of the same supercritical carbon dioxide extract as in Example 1-9 was dissolved. To the resulting solution, 50 mg of a strongly acidic cation exchange resin (AMBERLYST 15JW, manufactured by Dow Chemical Co.) was added and stirred, and then the resulting mixture was allowed to stand still at 60° C. for 1 day. The resin in the extract was filtered out to yield, as a filtrate, an extract treated with the 50% ethanol aqueous solution and the strongly acidic cation exchange resin (evaporation residue: 1.00 w/v %).

Comparative Example 2: Ethanol Solution of Supercritical Carbon Dioxide Extract

In ethanol (5 mL), 50.0 mg of the same supercritical carbon dioxide extract as in Example 1-9 was dissolved to yield an ethanol solution of the supercritical carbon dioxide.

Comparative Example 3: Extract Treated with 20% Ethanol Aqueous Solution and Strongly Acidic Cation Exchange Resin In a 20% ethanol aqueous solution (5 m L), 50.0 mg of the same supercritical carbon dioxide extract as in Example 1-9 was dissolved. To the resulting solution, 50 mg of a strongly acidic cation exchange resin (AMBERLYST 15JW, manufactured by Dow Chemical Co.) was added and stirred, and then the resulting mixture was allowed to stand still at 60° C. for 1 day. The resin in the extract was filtered out to yield, as a filtrate, an extract treated with the 20% ethanol aqueous solution and the strongly acidic cation exchange resin (evaporation residue: 1.00 w/v %).

Example 1-11: Extract Treated with Ethanol and Strongly Acidic Cation Exchange Resin In ethanol (5 mL), 50.0 mg of the residue obtained by molecular distillation of the supercritical carbon dioxide extract of seeds of nutmeg (*Myristica fragrans* Houtt., Myristicaceae) (purchased from PT MITRA AYU ADIPRATAMA) was dissolved. To the resulting solution, 50 mg of a strongly acidic cation exchange resin (AMBERLYST 15JW, manufactured by Dow Chemical Co.) was added and stirred, and then the resulting mixture was allowed to stand still at 60° C. for 1 day. The resin in the extract was filtered out to yield, as a filtrate, an extract treated with ethanol and the strongly acidic cation exchange resin (evaporation residue: 1.00 w/v %).

Example 1-12: Extract Treated with Cyclohexanol and Strongly Acidic Cation Exchange Resin In cyclohexanol (5 mL), 50.0 mg of the same distillation residue of the supercritical carbon dioxide extract as in Example 1-11 was dissolved. To the resulting solution, 50 mg of a strongly acidic cation exchange resin (AMBERLYST 15JW, manufactured by Dow Chemical Co.) was added and stirred, and then the resulting mixture was allowed to stand still at 60° C. for 1 day. The resin in the extract was filtered out to yield, as a filtrate, an extract treated with cyclohexanol and the strongly acidic cation exchange resin (evaporation residue: 1.00 w/v %).

Test Example 1: Evaluation of TRPM8 Activating Action

According to the following procedure, the $EC_{50}$ value in the TRPM8 activating action of a test sample was measured.
(1) Preparation of Cell Line Stably Expressing Human TRPM8
In order to prepare HEK293 cell line stably expressing human TRPM8, cloning of the human TRPM8 gene was performed. The full-length human TRPM8 gene was amplified from human prostate tissue total RNA (manufactured by COSMO BIO Co., Ltd.) by using RT-PCR method.

The obtained PCR product was cloned into an entry vector pENTR-D/TOPO (manufactured by Invitrogen Corp.), and then subcloned into pCDNA3.2-V5/DEST (manufactured by Invitrogen Corp.) and the vector was transduced into HEK293 cells by using Lipofectamine 2000 (manufactured by Invitrogen Corp.). The transduced cells were grown in a DMEM culture medium containing 450 μg/mL of G-418 (Promega Corp.), and then screened. The HEK293 cells do not express endogenous TRPM8, and hence can be used as a control for the TRPM8-transduced cell line.

(2) Calcium Imaging

The measurement of the activity of the TRPM8 transduced into the HEK293 cells was performed by a fluorescence calcium imaging method.

First, the cultured TRPM8 expressing cells were seeded (30,000 cells/well) to a poly-D-lysine coated 96-well plate (manufactured by BD Falcon, Inc.), and incubated at 37° C. overnight, and then the culture fluid was removed. Fluo4-AM solution (calcium kit II, manufactured by Dojindo Laboratories) was added to the cells and the cells were incubated at 37° C. for 30 to 60 minutes. Subsequently, the 96-well plate was set on a fluorescence plate reader (FDSS3000, manufactured by Hamamatsu Photonics K.K.), and while the inner temperature of the apparatus was maintained at 32° C., the fluorescence image due to Fluo4 when excited at an excitation wavelength of 480 nm was captured by using a CCD camera at a detection wavelength of 520 nm.

The measurement was performed every 1 second for 4 minutes in total. After 15 seconds were elapsed from the start of the measurement, any one of the test samples shown in Table 1 dissolved in Ringer's solution was added from a dispenser equipped in FDSS3000, and the activity of TRPM8 was evaluated based on the change of the fluorescence intensity.

(3) Evaluation of TRPM8 Activating Action

In order to eliminate the influence of the autofluorescence due to the test sample, the activity of TRPM8 was evaluated by subtracting the autofluorescence with the following formula.

Fluorescence intensity ($F_{sub}$) obtained by subtracting autofluorescence=(fluorescence intensity of TRPM8 expressing cell at each time point)−{(fluorescence intensity of HEK293 cell at each time point)−(fluorescence intensity of HEK293 cell at start of measurement)}

The TRPM8 activating action due to each sample was evaluated by using the peak of the fluorescence intensity ratio after the addition of the test sample. The fluorescence intensity ratio was calculated by using the following formula.

Fluorescence intensity ratio=$F_{sub}$ at each time point/fluorescence intensity of TRPM8 expressing cell at the start of the measurement The evaluation was performed with 2 wells for each treated group, and the average value of the 2 well evaluations was used.

(4) Evaluation Results of TRPM8 Activating Action

The TRPM8 activating action of each of the test samples shown in Table 1 was measured by using the foregoing method, within a final concentration ranging from 0.01 to 10 ppm, in terms of the dry solid content. From the measurement results, the dose response curve approximated to Hill equation was determined by using the least-squares method, and the $EC_{50}$ value was calculated from the curve. The $EC_{50}$ values in the TRPM8 activating action of the crude extract of Preparation Example 1, and the processed nutmeg products of Comparative Examples 1 to 3 and Examples 1-1 to 1-7 and 1-9 to 1-12 were shown in Table 1.

TABLE 1

|  | $EC_{50}$ (μg/mL) |
| --- | --- |
| Preparation Example 1 | 10.23 |
| Comparative Example 1 | 8.09 |
| Comparative Example 2 | 12.03 |
| Comparative Example 3 | 13.31 |
| Example 1-1 | 1.15 |
| Example 1-2 | 1.80 |
| Example 1-3 | 1.00 |
| Example 1-4 | 0.23 |
| Example 1-5 | 0.20 |
| Example 1-6 | 0.58 |
| Example 1-7 | 1.94 |
| Example 1-9 | 2.15 |
| Example 1-10 | 5.00 |
| Example 1-11 | 1.18 |
| Example 1-12 | 0.09 |

As shown in Table 1 presented above, the processed nutmeg products of Examples 1-1 to 1-7 and 1-9 to 1-12 exhibit excellent TRPM8 activating actions.

Test Example 2: Evaluation of Cooling Sensation of Mouthwashes Including Test Samples The mouthwashes (Test Products A, B and C) shown in Table 2 were prepared, the cooling sensation inducing effect was evaluated according to the following procedure and standards. The evaluation results are shown in FIG. 1.

TABLE 2

|  | Test Product A (Comparative Example 4) | Test Product B (Comparative Example 5) | Test Product C (Example 1-13) |
| --- | --- | --- | --- |
| Emanon CH-40 (Kao) | 0.12 g | 0.12 g | 0.12 g |
| Preparation Example 2 | — | 0.01 g | — |
| Example 1-8 | — | — | 0.01 g |
| Water (balance) | Amount resulting in total amount of 10 g | Amount resulting in total amount of 10 g | Amount resulting in total amount of 10 g |

(1) Evaluation Procedure

Five male panelists and one female panelist, six panelists in total, evaluated the cooling sensation induced with the mouthwashes.

Test Product A (Comparative Example 4), Test Product B (Comparative Example 5) or Test Product C (Example 1-13) was held in the mouth in an amount of 10 mL for 30 seconds and then spit out, and subsequently the cooling sensation sensed in the mouth during 30 minutes was evaluated based on grades of "0" to "5.0" (11-stage evaluation with a increment of 0.5). The respective test products were applied with an interval of 30 minutes or more between the successive test products.

(2) Evaluation Standards (Cooling Sensation Scores)
Grade 0: Nothing is sensed.
Grade 0.5
Grade 1.0: Cooling sensation is slightly sensed.
Grade 1.5
Grade 2.0: Faint cooling sensation is sensed.
Grade 2.5
Grade 3.0: Distinct cooling sensation is sensed.
Grade 3.5
Grade 4.0: Strong cooling sensation is sensed.
Grade 4.5
Grade 5.0: Extremely strong cooling sensation is sensed.
(3) Evaluation Results of Cooling Sensation Inducing Effect As shown in FIG. 1, the mouthwash of Example 1-13 exhibits a cooling sensation with high intensity and durability, as compared to the mouthwash of Comparative Example 4 and the mouthwash of Comparative Example 5 (a mouthwash including the sample of Preparation Example 2 in place of the sample of Example 1-8 wherein the concentrations of the samples were the same).

Example 2-1: Residue Obtained by Kugel Distillation (Simple Distillation) of Supercritical Carbon Dioxide Extract A two-stage Kugel distillation was performed for the component separation of 15.6 g of the supercritical carbon dioxide extract (purchased from PT MITRA AYU ADIPRATAMA) of seeds of nutmeg (*Myristica fragrans* Houtt., Myristicaceae). The first stage was performed at a pressure reduction degree of 0.8 mmHg and a temperature of 80° C. to yield a fraction (1) of 5.23 g and a distillation residue (1) of 7.91 g (loss: 2.46 g). The second stage was performed at a pressure reduction degree of 0.006 mmHg and a temperature of 120° C. to yield, from the distillation residue (1), a fraction (2) of 2.39 g and a distillation residue (2) of 5.19 g (loss: 0.33 g).

Example 2-2: Residue Obtained by Kugel Distillation (Simple Distillation) of EtOH Extract To 160 g of crushed seeds of nutmeg (*Myristica fragrans* Houtt., Myristicaceae), 1.6 L of 99.5 vol % ethanol was added, the crushed seeds were soaked and extracted at room temperature for 3 days, and then the crushed seeds were filtered out to prepare a crude extract. Successively, the crude extract was concentrated with an evaporator to yield 19.49 g of an EtOH extract, and 7.59 g of the EtOH extract was subjected to component separation by a two-stage Kugel distillation. The first stage was performed at a pressure reduction degree of 0.8 mmHg and a temperature of 80° C. to yield a fraction (3) of 0.09 g and a distillation residue (3) of 7.05 g (loss: 0.45 g). The second stage was performed at a pressure reduction degree of 0.01 mmHg and a temperature of 130° C. to yield, from the distillation residue (3), a fraction (4) of 1.31 g and a distillation residue (4) of 5.62 g (loss: 0.12 g).

Example 2-3: Residue Obtained by Fractional Distillation and Molecular Distillation of Supercritical Carbon Dioxide Extract A fractional distillation of 234 kg of a supercritical carbon dioxide extract (purchased from PT MITRA AYU ADIPRATAMA) of seeds of nutmeg (*Myristica fragrans* Houtt., Myristicaceae) was performed under the conditions of a pressure reduction degree of 1.5 mmHg and a temperature of 80° C. to yield a fraction (5) of 76.5 kg and a distillation residue (5) of 151.5 kg (loss: 6 kg). Successively, 132.6 kg of the distillation residue (5) was subjected to component separation by a three-stage molecular distillation. The first stage was performed at a pressure reduction degree of 0.375 mmHg and a temperature of 60° C. to yield, from the distillation residue (5), a fraction (6) of 27.5 kg. The second stage was performed at a pressure reduction degree of 0.00075 mmHg and a temperature of 80° C. to yield, from the distillation residue of the first stage, a fraction (7) of 29.3 kg. The third stage was performed at a pressure reduction degree of 0.00075 mmHg and a temperature of 120° C. to yield, from the distillation residue of the second stage, a fraction (8) of 16.9 kg and a distillation residue (6) of 55.3 kg (third stage loss: 3.6 kg).

Test Example 3: Evaluation of TRPM8 Activating Action

The distillation residues (1), (2), (4) and (6), the fractions (1) and (2), the supercritical carbon dioxide extract purchased from PT MITRA AYU ADIPRATAMA, and the EtOH extract prepared in Example 2-2 were each used as a test sample, and the $EC_{50}$ values in the TRPM8 activating action were measured according to the following procedure.

(1) Preparation of Cell Line Stably Expressing Human TRPM8

In order to prepare HEK293 cell line stably expressing human TRPM8, cloning of the human TRPM8 gene was performed. The full-length human TRPM8 gene was amplified from human prostate tissue total RNA (manufactured by COSMO BIO Co., Ltd.) by using RT-PCR method.

The obtained PCR product was cloned into an entry vector pENTR-D/TOPO (manufactured by Invitrogen Corp.), and then subcloned into pCDNA3.2-V5/DEST (manufactured by Invitrogen Corp.) and the vector was transduced into HEK293 cells by using Lipofectamine 2000 (manufactured by Invitrogen Corp.). The transduced cells were grown in a DMEM culture medium containing 450 µg/mL of G-418 (Promega Corp.), and then screened. The HEK293 cells do not express endogenous TRPM8, and hence can be used as a control for the TRPM8-transduced cell line.

(2) Calcium Imaging

The measurement of the activity of the TRPM8 transduced into the HEK293 cells was performed by a fluorescence calcium imaging method.

First, the cultured TRPM8 expressing cells were seeded (30,000 cells/well) to a poly-D-lysine coated 96-well plate (manufactured by BD Falcon, Inc.), and incubated at 37° C. overnight, and then the culture fluid was removed. Fluo4-AM solution (calcium kit II, manufactured by Dojindo Laboratories) was added to the cells and the cells were incubated at 37° C. for 30 to 60 minutes. Subsequently, the 96-well plate was set on a fluorescence plate reader (FDSS3000, manufactured by Hamamatsu Photonics K.K.), and while the inner temperature of the apparatus was maintained at 32° C., the fluorescence image due to Fluo4 when excited at an excitation wavelength of 480 nm was captured by using a CCD camera at a detection wavelength of 520 nm.

The measurement was performed every 1 second for 4 minutes in total. After 15 seconds were elapsed from the start of the measurement, any one of the test samples (prepared by dissolving the samples shown in Table 1 presented below in Ringer's solution) was added from a dispenser equipped in FDSS3000, and the activity of TRPM8 was evaluated based on the change of the fluorescence intensity.

(3) Evaluation of TRPM8 Activating Action

In order to eliminate the influence of the autofluorescence due to the test sample, the activity of TRPM8 was evaluated by subtracting the autofluorescence with the following formula.

Fluorescence intensity ($F_{sub}$) obtained by subtracting autofluorescence=(fluorescence intensity of TRPM8 expressing cell at each time point)–{(fluorescence intensity of HEK293 cell at each time point)–(fluorescence intensity of HEK293 cell at start of measurement)}

The TRPM8 activating action due to each sample was evaluated by using the peak of the fluorescence intensity ratio after the addition of the test sample. The fluorescence intensity ratio was calculated by using the following formula.

Fluorescence intensity ratio=$F_{sub}$ at each time point/$F_{sub}$ at start of measurement The evaluation was performed with 2 wells for each treated group, and the average value of the 2 well evaluations was used.

(4) Evaluation Results of TRPM8 Activating Action

The TRPM8 activating action of each of the test samples was evaluated within a final concentration ranging from 0.1 ppm to 30 ppm, and the dose response curve approximated to Hill equation was determined by using the least-squares method. The $EC_{50}$ values in the TRPM8 activating action of the test samples calculated from the resulting curve are shown below.

TABLE 3

| Sample | $EC_{50}$ (µg/mL) |
|---|---|
| Distillation residue (1) | 10.3 |
| Distillation residue (2) | 4.0 |
| Distillation residue (4) | 7.9 |
| Distillation residue (6) | 3.3 |
| Supercritical carbon dioxide extract | 18.2 |
| EtOH extract | 21.0 |

The fraction (1) and the fraction (2) were found to have no TRPM8 activating action even at a final concentration of 30 ppm.

As shown in Table 1 presented above, the distillation residues (1), (2), (4) and (6) each have an excellent TRPM8 activating action.

The invention claimed is:

1. A method for producing a processed nutmeg product, comprising simultaneously treating nutmeg or an extract thereof with an alcohol or a 25% (v/v) or more alcohol aqueous solution and at least one member selected from the group consisting of a protonic acid and an H-type cation exchange resin.

2. The production method according to claim 1, wherein said alcohol is an alcohol having from 1 to 10 carbon atoms.

3. The production method according to claim 1, wherein the H-type cation exchange resin is a strongly acidic H-type cation exchange resin.

4. The method of claim 1, wherein the nutmeg or extract thereof comprises nutmeg seeds and/or nutmeg mace.

5. The method of claim 1, further comprising drying and subsequently cutting or crushing nutmeg prior to treating the nutmeg.

6. The method of claim 1, further comprising extracting a nutmeg extract from nutmeg prior to treating the nutmeg extract.

7. The method of claim 6, wherein the extracting comprises distillation.

8. The method of claim 6, wherein the extracting comprises extraction with a liquid mixture comprising water and a polar solvent.

9. The method of claim 6, wherein the extracting comprises extraction with from 1 to 50 parts by mass of extraction solvent, in relation to 1 part by mass of nutmeg.

10. The method of claim 6, wherein the extracting is performed at a temperature of 3° C. or higher and for a time of at least 1 hour and at normal or elevated pressure.

11. The method of claim 1, wherein the alcohol or an alcohol in the aqueous solution is a monohydric alcohol.

12. The method of claim 1, wherein from 0.1 to 1000 parts by mass of the alcohol are present during the treating, with respect to 1 part by mass of the nutmeg.

13. The method of claim 1, wherein the treating of the nutmeg or extract thereof is at a temperature of from 3 to 100° C. for a time of from 0.1 hour to 5 days.

14. The method of claim 1, further comprising diluting the processed nutmeg product, concentrating the processed nutmeg product, freeze-drying the processed nutmeg product, preparing the processed nutmeg product as a powder, and/or preparing the processed nutmeg product as a paste.

15. The method of claim 1, wherein treating the nutmeg or extract thereof comprises treating with the H-type cation exchange resin.

16. A method for imparting a cooling sensation, comprising
producing a processed nutmeg product by the method of claim 1, and
administering, to a subject in need thereof, the processed nutmeg product.

17. A method for activating TRPM8, comprising
producing a processed nutmeg product by the method of claim 1, and
administering, to a subject in need thereof, the processed nutmeg product.

* * * * *